(12) United States Patent
Porret et al.

(10) Patent No.: US 7,431,157 B2
(45) Date of Patent: Oct. 7, 2008

(54) PACKAGE FOR STERILE PRODUCTS

(75) Inventors: Jean-Yves Porret, Gieres (FR); Hubert Jansen, Michelbach (DE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 531 days.

(21) Appl. No.: 10/485,929

(22) PCT Filed: Nov. 16, 2001
(Under 37 CFR 1.47)

(86) PCT No.: PCT/FR01/03613

§ 371 (c)(1),
(2), (4) Date: Mar. 28, 2005

(87) PCT Pub. No.: WO02/40064

PCT Pub. Date: May 23, 2002

(65) Prior Publication Data

US 2006/0054523 A1    Mar. 16, 2006

(30) Foreign Application Priority Data

Nov. 20, 2000 (FR) .................................. 00 14975

(51) Int. Cl.
*A61B 19/02* (2006.01)
(52) U.S. Cl. .................. 206/439; 206/363; 206/366; 206/370; 53/432

(58) Field of Classification Search ................. 206/438, 206/439, 363–370, 484.1, 524.6; 53/396, 53/428, 432; 422/292–300
See application file for complete search history.

(56) References Cited

U.S. PATENT DOCUMENTS

| | | | | |
|---|---|---|---|---|
| 4,884,694 A | * | 12/1989 | Sengewald | 206/484.1 |
| 5,342,673 A | * | 8/1994 | Bowman et al. | 428/198 |
| 5,830,547 A | * | 11/1998 | MacKenzie et al. | 428/36.1 |
| 6,164,044 A | * | 12/2000 | Porfano et al. | 53/471 |
| 6,228,324 B1 | * | 5/2001 | Hasegawa et al. | 422/30 |
| 6,629,602 B1 | * | 10/2003 | Heyman | 206/438 |

* cited by examiner

*Primary Examiner*—David T. Fidei
(74) *Attorney, Agent, or Firm*—David M. Fortunato; Hoffman & Baron, LLP

(57) ABSTRACT

This packaging for sterile products or products intended to be sterilized by a gas, for example a gas of the ETO type, comprises a tub (2) made of plastic and a cover sheet (14) made of selectively impervious material, fixed to the tub (2) so as to seal the latter imperviously.

According to the invention, the packaging comprises a screen (20, 22; 24, 26; 26) against electron radiation (E), placed along the cover sheet (14) on the inside of the tub (2) and dimensioned in such a way as to extend above the products (10) to be sterilized and so as to delimit on the cover sheet (14) a peripheral zone (14a) for fixing this cover sheet (14) to the tub (2).

18 Claims, 4 Drawing Sheets

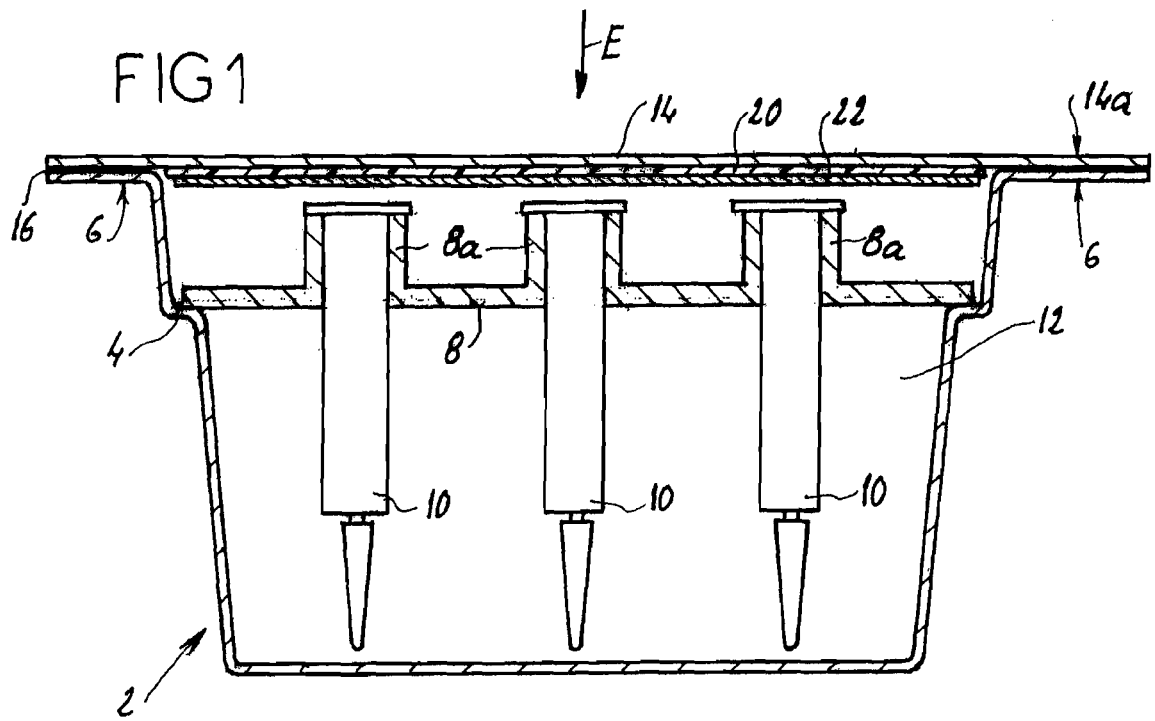
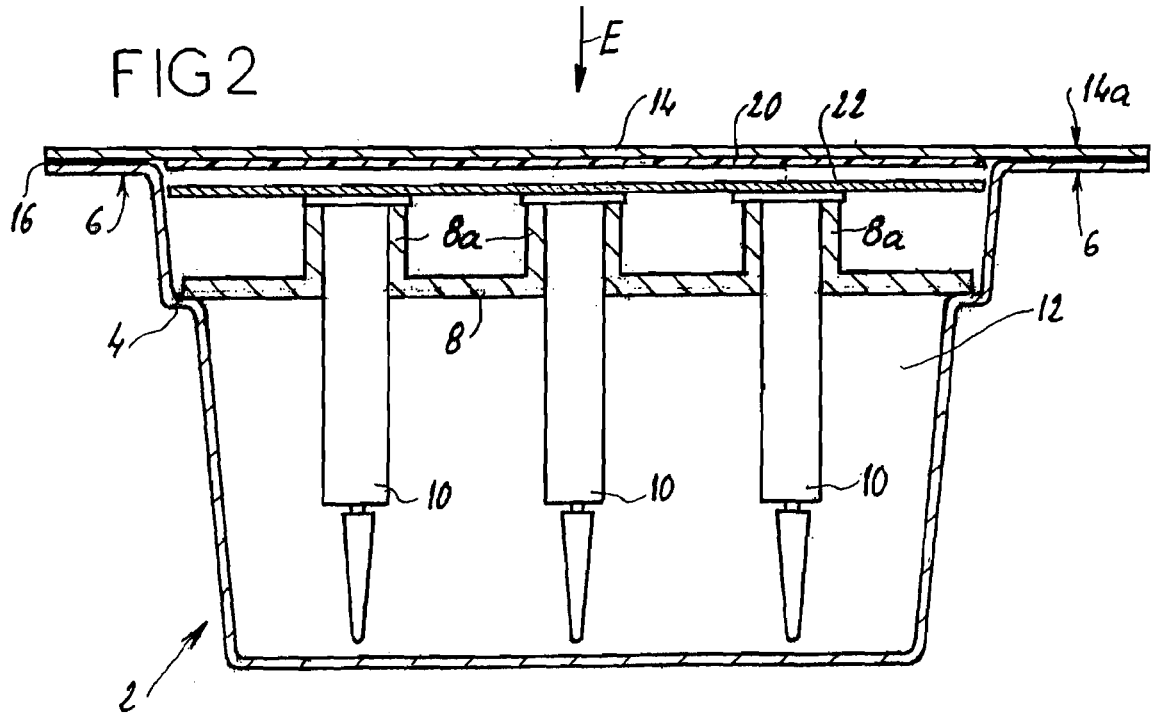

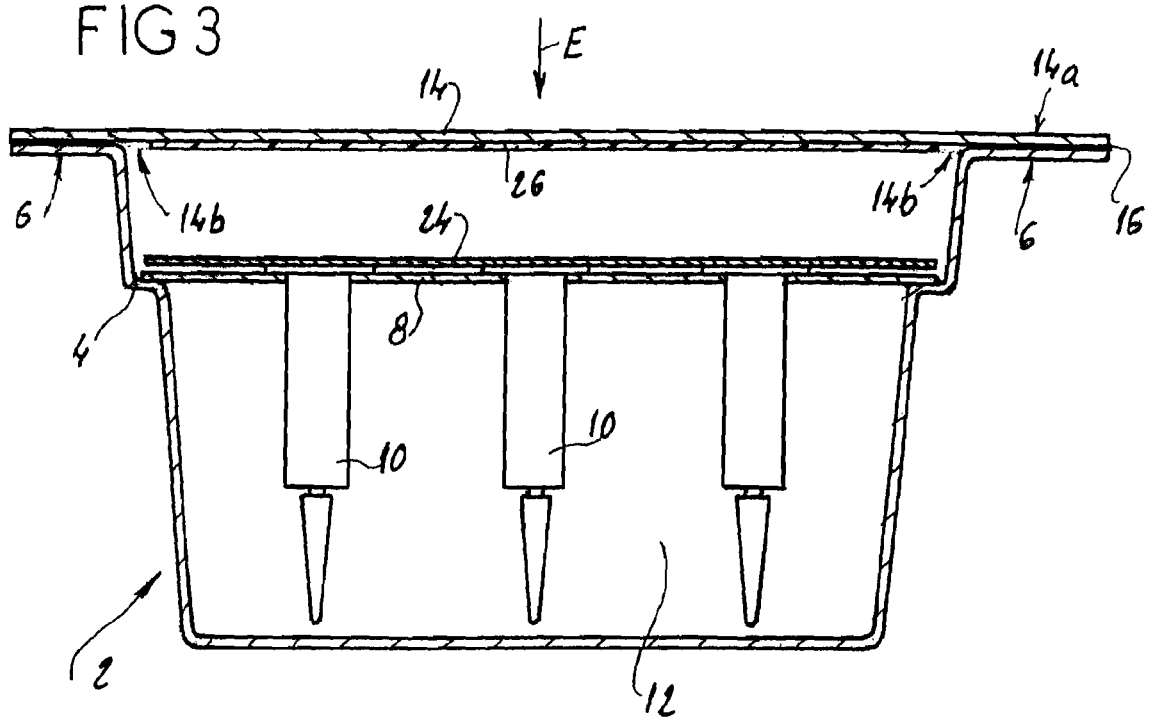
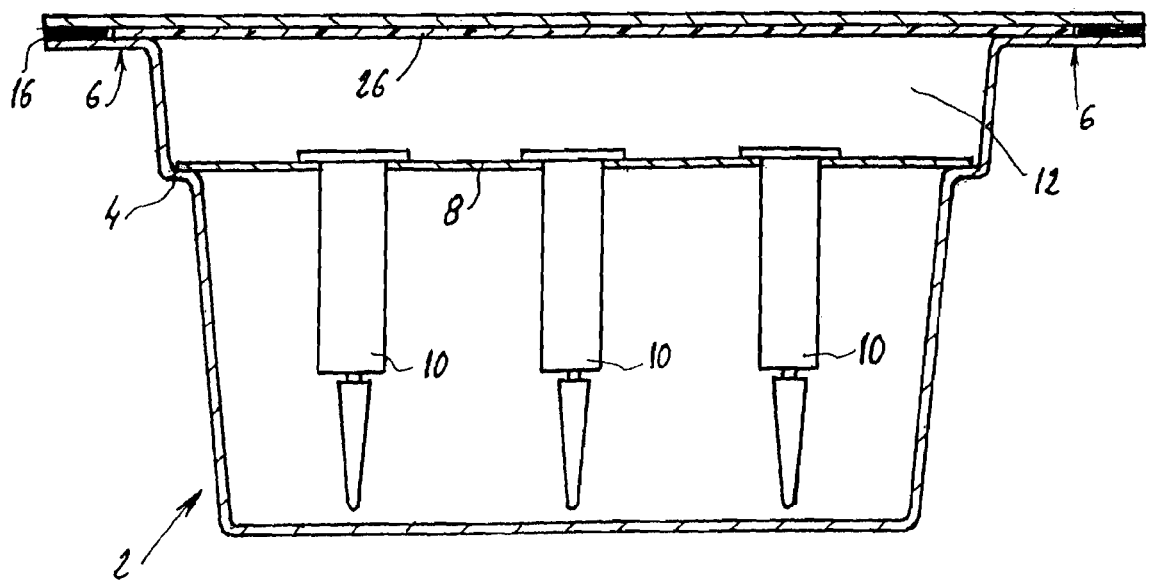

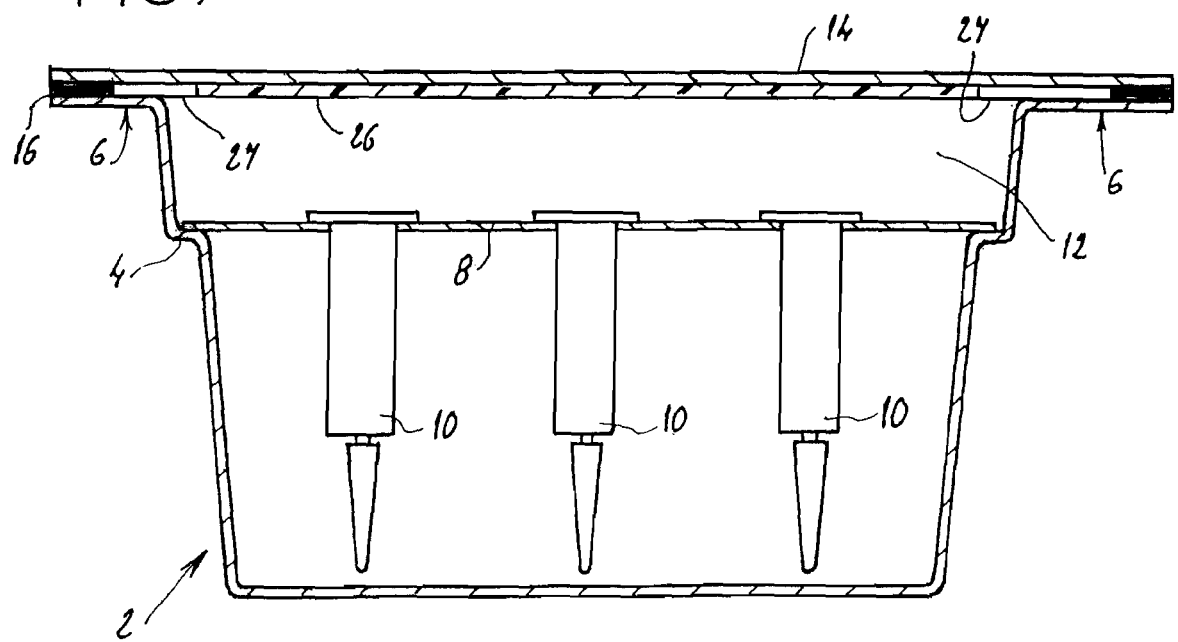

PACKAGE FOR STERILE PRODUCTS

The present invention relates to the field of sterile/sterilized packaging and more particularly to packaging intended to be used to transport sterilized products or products intended to be used to be sterilized.

The conditions of sterility in which certain stages of the handling or transportation of products or instruments intended for medical use are to be performed are extremely strict, particularly in the pharmaceutical industry. It is therefore extremely important to produce packaging compatible with such requirements.

In the remainder of the description, mention will be made of a selectively impervious material, which we need to define.

The expression "selectively impervious" as used in the present description and in the Claims, is to be understood as meaning that the material is designed, in terms of structure, to control any exchange between the inside of the packaging and its external environment. This means, among other things, that the packaging is impervious, individually or in combination, to contamination by micro-organisms, bacteria and/or a biologically active material likely to come into contact with the packaging while it is being handled, while at the same time remaining permeable to a sterilization or decontamination gas, for example of the ETO (ethylene oxide) type.

Mention will also be made of a "material that forms a screen against electron radiation", which is to be understood as being a material capable of reflecting and/or partially or completely absorbing the kinetic energy of the electrons from an electron beam, and therefore of slowing or even preventing these electrons from passing through the said material.

The expressions "plastic" and "plastics material" are to be understood as meaning any material chosen from the polymer families such as styrenes, acrylics, polysulfones, polycarbonates, polyesters, polyolefins, etc., including copolymers and polymer combinations and alloys.

Packaging for sterile products or products intended to be sterilized by a gas of the ETO type and comprising a tub made of plastic and a cover sheet made of a selectively impervious material bonded onto the tub so as to seal the latter is known.

The production of packaging for products intended to be sterilized by a gas, for example of the ETO type, by a method consisting in using a tub made of plastic and a cover sheet made of a selectively impervious material and in sealing the tub imperviously by fixing the peripheral edge of the cover sheet to the tub is also known.

Certain types of packaging such as those used for transporting syringes before they are filled with an active product or drug, are currently transported in plastic boxes, for example made of polystyrene, covered with a cover sheet made of a selectively impervious material.

The latter is, for example, a sheet based on filaments of HDPE (high density polyethylene) or some other polymer, bound together especially by heat and pressure. A product such as this is marketed, for example, under the trade mark TYVEK®. Products intended to be sterilized are placed inside a box, which is then sealed with the selectively impervious sheet. The sterilization gas, for example of the ETO type, then enters the box through the sheet of selectively impervious material. The tub containing the sterilized products is then placed in a protective bag so that the said tub can be transported. By way of example, a tub or packaging such as this may contain syringes intended to be filled with a drug in a sterile room or controlled-environment room. It is also possible for the packaging to be placed beforehand in a protective bag which has a window closed with a material that is permeable to the sterilization gas, and for the said sterilization to be performed thereafter.

Before the said syringes are filled, the protective bag needs to be opened and the packaging, which may be contaminated, needs to be decontaminated before it is taken, for example, into a sterile room. Such decontamination can be achieved using multidirectional irradiation by an electron beam developing enough energy that when it has passed through the cover sheet, it delivers a dose of irradiation of, for example, 25 kGy. This means that it can be taken that the selectively impervious material has been decontaminated throughout its thickness, particularly the sealed zone, at the interface between the tub and the said material. As far as the rest is concerned, the combination of the density and thickness of the packaging is such that it stops these electrons.

This type of decontamination is not, however, suitable for every type of product transported in the packaging. This is because the electron beam passing through the sheet of selectively impervious material carries the risk, on the one hand, of altering or adversely affecting the material of which the syringes or products placed in the tub are made, for example glass, and on the other hand, of using the oxygen in the air contained in the said tub to generate ozone which carries the risk, on the one hand, of adversely affecting the active products used to fill the syringes and/or, for example, the rubber components present in the box such as the caps on the needles mounted on the syringes, for example, and on the other hand, of polluting the atmosphere.

The objective of the present invention is to provide packaging for products or instruments intended to be sterilized, so that an electron beam can be used to carry out biological decontamination of this packaging before it is taken into a sterile room or controlled-environment room without the products or instruments located inside the packaging being adversely affected.

The objective of the present invention is also to provide a method for producing packaging for products or instruments intended to be sterilized, the said packaging being compatible with sterilization, for example, using a gas of the ETO type, on the one hand, and with decontamination using an electron beam, on the other hand.

According to the invention, the packaging comprises a screen against electron radiation, placed along the cover sheet on the inside of the tub and dimensioned so as to extend above the products to be sterilized and so as to delimit on the cover sheet a peripheral zone for fixing this cover sheet to the tub.

According to the invention, the method consists in:

using a screen against electron radiation, choosing the shape and dimensions of this screen in such a way that this screen extends, when in the tub, above the products to be sterilized and delimits on the cover sheet a peripheral zone for fixing this cover sheet to the tub.

The screen may be attached to the cover sheet in particular by bonding or welding, or may be simply arranged over the products inside the tub, prior to the sealing of the latter. The screen may also be formed of at least two sheets or layers, at least one of the said sheets or layers then being attached to the cover sheet whereas at least one other of the said sheets or layers is arranged inside the tub, prior to the sealing of the latter, either over the products or on ledges provided for this purpose or on a product positioning piece placed in this tub.

The screen may comprise a metallized or metal sheet, a plastic material, a material based on natural fibres, for example plant fibres, or at least two complementary sheets of selectively impervious material.

The selectively impervious material may be a material based on filaments of HDPE or some other polymer, bound together by heat and pressure, or a material based on plant fibres, for example paper.

Other features and advantages will also become apparent from the detailed description given hereinafter, given by way of example with reference to the appended drawing, in which:

FIG. 1 is a view in section of packaging according to the invention;

FIG. 2 is a view similar to FIG. 1 of packaging according to an alternative form of embodiment;

FIG. 3 is a view similar to FIG. 1 of packaging according to another alternative form of embodiment;

FIG. 4 depicts another example of packaging according to the invention;

FIG. 7 depicts another example of packaging according to the invention.

Figure 5:
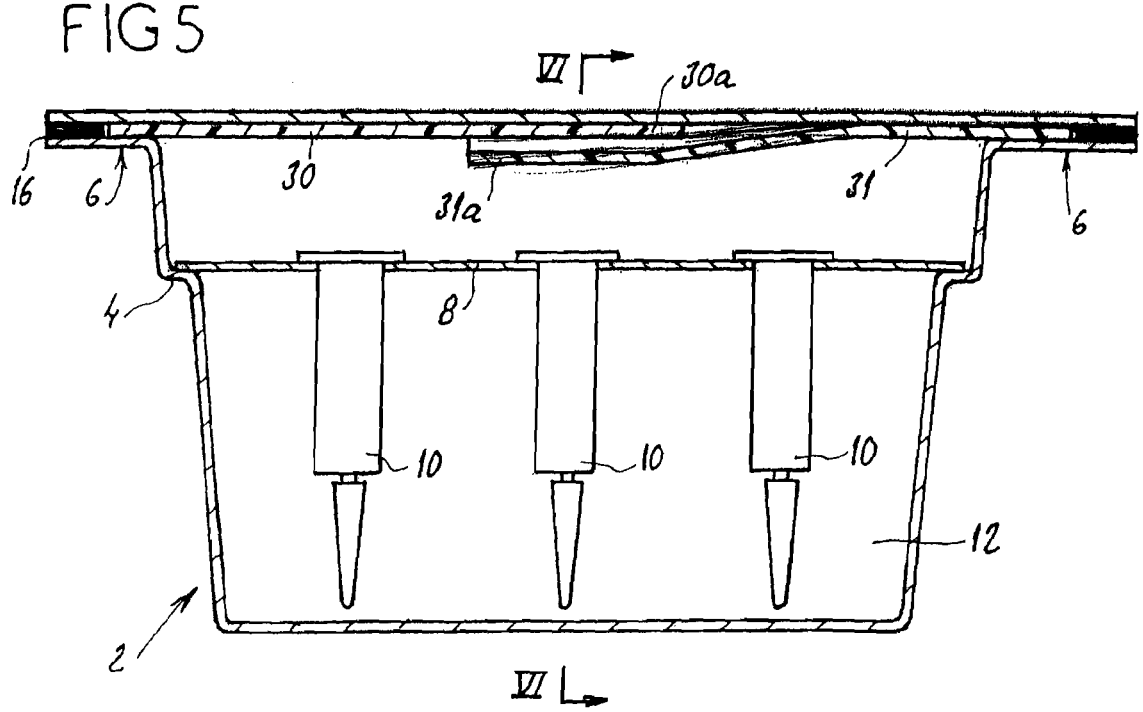
FIG. 5 depicts an additional example of packaging according to the invention.

The packaging according to the invention, depicted in FIGS. 1 and 2, comprises a tub 2 made of plastic, for example polystyrene, with an internal peripheral shoulder 4 and an external peripheral rim 6 extending essentially horizontally at the upper end of the tub. The shoulder 4, whose distance away from the bottom of the tub 2 can be chosen, allows a support 8 to be rested on it. This support 8, which may comprise hollow shafts 8a for positioning the syringes 10, as shown in FIG. 1 or 2, or may consist of a perforated plate, as shown in FIGS. 3 to 7, allows the syringes 10 to be held in place.

The interior volume of the packaging is denoted by the reference 12.

The packaging also comprises a cover sheet 14 made of a selectively impervious material and fixed by its peripheral zone 14a on the peripheral rim 6 of the tub 2. A layer of adhesive 16 producing the interface between the cover sheet 14 and the peripheral rim 6 allows the tub 2 to be sealed imperviously in accordance with the invention. According to another embodiment, the layer of adhesive 16 may be replaced by any other means of impervious connection, such as a weld.

In the exemplary embodiment depicted in FIG. 1, the packaging also comprises two additional sheets 20, 22 attached to the cover sheet 14, on the inside of the tub 2, and made of a selectively impervious material. The shape and dimensions of these complementary sheets 20, 22 are such that they make it possible to delimit, on the said cover sheet 14, the peripheral zone 14a for fixing to the tub 2. This peripheral zone 14a thus has a thickness corresponding to that of the cover sheet 14, while the central zone of the cover sheet 14 has a thickness of coverage corresponding to that of an assembly of three sheets of a selectively impervious material. This assembly is obtained, for example, by bonding.

Packaging such a this has the advantage that the covering means thus produced, consisting of the cover sheet 14 and of the complementary sheets 20, 22 remains entirely permeable to the sterilizing gas ETO. By contrast, the thickness obtained in its central zone, corresponding to an assembly of three selectively impervious sheets, means that the energy of the electrons from an electron beam used for decontamination, depicted diagrammatically by the arrow "E" in the figures and adjusted to provide a dose of irradiation of, for example, 25 kGy under the cover sheet 14 can be substantially absorbed. The arrow "E" diagrammatically depicts the electron radiation towards the cover sheet 14, but the irradiation of the packaging according to the invention is multidirectional and comes from all directions so that it reaches every side of the said packaging. The material of which the tub 2 is made has a combination of density and thickness such that it is practically able to prevent the electrons from this decontamination beam from passing through it. This dose is needed to obtain decontamination through the cover sheet 14, particularly as far as the layer of adhesive 16 that forms the interface between the said cover sheet 14 and the tub 2. The electron beam advantageously allows the selectively impervious material to be decontaminated as far as the peripheral end (outer edge) thereof. The complementary sheets 20, 22 are capable of absorbing enough of the energy of the electrons that might pass through the cover sheet 14 so that they do not adversely affect or carry the risk of adversely affecting the products inside the packaging, on the one hand, and that they do not generate ozone inside the interior volume 12, on the other hand.

When, by way of a screen, sheets such as TYVEK® are used, there are, for example, two complementary sheets 20, 22.

It is also possible to cover the syringes 10 arranged in the tub 2 with one or more protective sheets 24, for example made of selectively impervious material.

In the alternative form depicted in FIG. 2, the sheet 22 is not secured to the sheet 20 but rests on the syringes 10.

In the packaging according to FIG. 3, the screen consists of a metallic sheet 26, a metallized sheet or a sheet made of plastic. A sheet of aluminium or of stainless steel may thus be attached to the cover sheet 14.

The protective sheet 24 may also be used in this exemplary embodiment.

According to another embodiment of the packaging according to the invention, not depicted in the figures, the screen may consist of the protective sheet 24 itself. The screen is thus arranged on the syringes 10 inside the tub 2, prior to the sealing of the latter, and is free in part of the interior volume 12 delimited by the cover sheet 14 and the shoulder 4. The protective sheet 24 may be produced from the same materials as those used to produce the sheet forming a screen 26, or with two sheets of selectively impervious material. Packaging such as this is very advantageous when the tub 2, sealed by the cover sheet 14, is turned over during the decontamination operation. After turning over, the screen rests on the inside of the cover sheet 14 and thus restricts or prevents the penetration of electrons into the interior volume 12 and therefore restricts or prevents the creation of ozone.

Other known materials capable of absorbing and/or of reflecting the kinetic energy of the electrons emitted by a decontamination beam may also be used to produce packaging according to the invention. Fibres of natural origin, for example plant fibres (cellulose, paper) may thus be used to produce the screen. In general, the material of which the screen is made has density and thickness characteristics that allow it to substantially absorb a dose of electron irradiation of 25 kGy. The energy of the electrons capable of passing through the screen is practically reduced to zero.

FIG. 4 thus shows an exemplary embodiment in which the sheet forming a screen 26 consists of a selectively impervious material whose density/thickness ratio allows it to absorb the aforementioned dose of electron irradiation. The dimensions and the shapes of the sheet forming a screen 26 are chosen to allow it to rest via its periphery on part of the peripheral ledge 6. The sheet forming a screen 26 is fixed, for example, by any means to the cover sheet 14.

In the example of FIG. 3, the sheet forming a screen 26 has dimensions and a form which allows it to make a peripheral slot 14b between itself and the tub 2, thus making it easier for the sterilizing gas to penetrate the interior volume 12.

According to one embodiment of the packaging according to the invention, it is also possible to use a sheet forming a screen 26 which is made of an impervious material as depicted in FIG. 7. The sheet forming a screen 26 then rests on the peripheral rim 6 and has openings 27 distributed discretely on its periphery. The openings 27 thus allow the sterilizing gas to penetrate the interior volume 12, electron radiation, capable of passing through the relatively small-sized openings 27, having only a minimum impact on the products arranged inside the tub 2.

Figure 6:
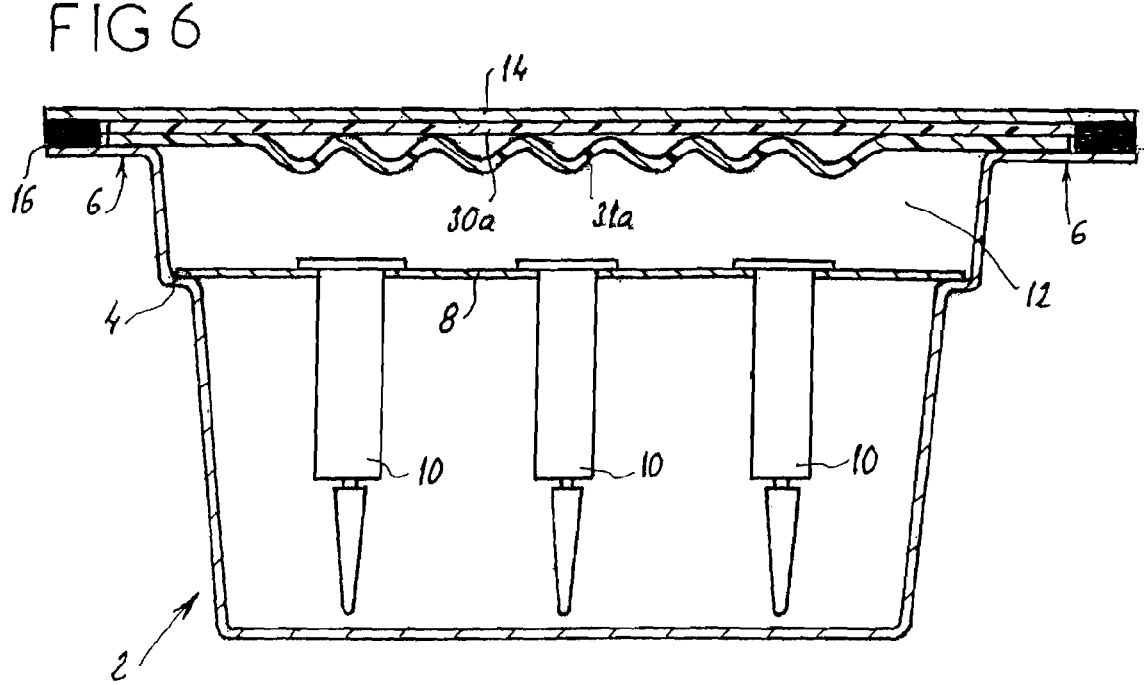
FIG. 6 is a view of packaging of FIG. 4 in section on VI-VI.

The exemplary embodiment depicted in FIGS. 5 and 6 comprises two half sheets 30, 31, the outer edges of which rest on the peripheral rim 6 and the inner edges 30a, 31a of which overlap. One of the half sheets 31a has a corrugated shape so as to form passages for the sterilizing gas, particularly when the material of which the two half sheets 30, 31 are made is impervious. Each of the half sheets 30, 31 constitutes a screen to electron radiation. In the outer periphery of the overlapping zone there is a local increase in thickness between the peripheral rim 6 and the cover sheet 14, which is compensated for, for example, by a layer of adhesive 16 which is locally thicker. This is of no impediment in so far as the decontamination electron radiation passing through the cover sheet 14 is capable of reaching any irregularity there might be in the said layer of adhesive 16.

Any other association or transposition of technical elements from one exemplary embodiment to another may be envisaged, provided that it results in a cover assembly which is selectively impervious and capable of absorbing a dose of electron irradiation of, for example, 25 kGy.

The present invention also relates to a method for producing packaging for products intended to be sterilized by a gas, for example of the ETO type. The method consists in using the tub 2 made of plastic and the cover sheet 14 made of selectively impervious material and in sealing the said tub 2 by fixing the peripheral edge 14a of the cover sheet 14 to the tub 2.

According to the invention, the method consists in choosing the shape and dimensions of this material to delimit, by attaching it to the cover sheet 14, on the one hand, a peripheral edge 14a, the thickness of which is that of the said cover sheet 14 and, on the other hand, a central zone, the thickness of which corresponds to that of an assembly of the cover sheet 14 and of the screen.

Producing a cover means such as this to seal the tub 2 is particularly advantageous in so far as the properties of the cover sheet 14 made of selectively impervious material are maintained in spite of the addition of a screen against electron radiation. This advantage is particularly beneficial when two complementary selectively impervious sheets are being used to make the screen.

According to an alternative form according to the invention, the screen may be attached and fixed to the cover sheet 14 by thermal, high-frequency, ultrasonic or vibration welding, or some other type of welding, or else by goffering or by use of rivets.

The same is true of the assembly of the cover sheet 14 with the complementary sheet or sheets.

According to one embodiment of the packaging according to the invention, the cover sheet 14 may be made with a microperforated membrane.

According to an alternative form of the method according to the invention, it is possible to place the screen over the products inside the tub 2 prior to sealing the tub 2.

The invention claimed is:

1. Packaging for sterile products or products intended to be sterilized by a gas, said packaging comprising a tub (2) made of plastic and a cover sheet (14) made of a selectively impervious material, fixed to the tub (2) so as to seal the latter imperviously;

characterized in that said packaging comprises a screen (20, 22; 24, 26; 26) against electron radiation (E), placed along the cover sheet (14) on the inside of the tub (2) and dimensioned so as to extend above the products (10) to be sterilized and so as to delimit a peripheral zone (14a) for fixing the cover sheet (14) to the tub (2);

wherein the screen (20, 22; 24, 26) is formed of at least two sheets or layers and in that at least one of the said sheets or layers (20; 26) is attached to the cover sheet (14), whereas at least one other of the said sheets or layers (22; 24) is arranged inside the tub (2) prior to the sealing of the latter, either over the products (10) or on ledges provided for that purpose or on a product-positioning piece placed in this tub.

2. Packaging according to claim 1, characterized in that at least one of said sheets or layers of the screen (20, 22; 26) is attached to the cover sheet (14) by bonding or welding.

3. Packaging according to claim 1, characterized in that the screen (24; 26) is a metallized or metallic sheet (26).

4. Packaging according to claim 1, characterized in that the screen comprises a plastic material.

5. Packaging according to claim 1, characterized in that the screen comprises a material based on natural fibres.

6. Packaging according to claim 1, characterized in that the screen comprises at least two complementary sheets (20, 22) of selectively impervious material.

7. Packaging according to claim 1, characterized in that the selectively impervious material is a material based on filaments of HDPE or some other polymer, bound together by heat and pressure.

8. Packaging according to claim 1, characterized in that the selectively impervious material is a material based on plant fibres.

9. Method for producing packaging for sterile products or products intended to be sterilized by a gas, said method comprising the steps of:

using a tub (2) made of plastic and a cover sheet (14) made of selectively impervious material;

sealing the tub (2) imperviously by fixing the peripheral zone (14a) of the cover sheet (14) to the tub (2);

using a screen (20, 22; 26, 24; 26) formed by at least two sheets or layers against electron radiation (E), attaching at least one of the said sheets or layers (20; 26) to the cover sheet (14) and in arranging at least one other of the said sheets or layers (22; 24) inside the tub (2) prior to the sealing of the latter, either over the products (10) or on ledges provided for this purpose, or on a product-positioning piece placed in this tub, choosing the shape and dimensions of this screen (20, 22; 26, 24; 26) in such a way that this screen (20, 22; 26, 24; 26) extends, when in the tub (2), above the products (10) to be sterilized and delimits, on the cover sheet (14), the said peripheral zone (14a).

10. Method according to claim 9, characterized in that the step of attaching at least one of said sheets or layers of the screen (20, 22; 26) to the cover sheet (14) is conducted by bonding or welding.

11. Packaging according to claim 1, characterized in that said gas is of the ETO type.

12. Packaging according to claim 5, characterized in that said natural fibres include plant fibres.

13. Packaging according to claim 8, characterized in that said plant fibres include paper.

14. Method according to claim 9, characterized in that said gas is of the ETO type.

15. Packaging for sterile products or products intended to be sterilized by a gas, said packaging comprising a tub (2) made of plastic and a cover sheet (14) made of a selectively impervious material, fixed to the tub (2) so as to seal the latter imperviously;

characterized in that said packaging comprises a screen (20, 22; 24, 26; 26) against electron radiation (E), placed along the cover sheet (14) on the inside of the tub (2) and dimensioned so as to extend above the products (10) to be sterilized and so as to delimit a peripheral zone (14*a*) for fixing the cover sheet (14) to the tub (2);

wherein the screen comprises at least two complementary sheets (20, 22) of selectively impervious material.

16. Packaging according to claim 15, characterized in that the selectively impervious material is a material based on filaments of HDPE or some other polymer, bound together by heat and pressure.

17. Packaging according to claim 15, characterized in that the selectively impervious material is a material based on plant fibres.

18. Packaging according to claim 17, characterized in that said plant fibres include paper.

* * * * *